(12) United States Patent
Böhling et al.

(10) Patent No.: US 9,156,802 B2
(45) Date of Patent: *Oct. 13, 2015

(54) SEPARATING OFF 5-HYDROXYMETHYLFURFURAL (HMF) FROM REACTION SOLUTIONS BY STEAM DISTILLATION

(71) Applicant: BASF SE, Ludwigshafen (DE)

(72) Inventors: Ralf Böhling, Lorsch (DE); Benoit Blank, Mannheim (DE); Alois Kindler, Grünstadt (DE); Carmen Feldner, Ludwigshafen (DE); Sandra Umlauf, Bad Dürkheim (DE)

(73) Assignee: BASF SE (DE)

( * ) Notice: Subject to any disclaimer, the term of this patent is extended or adjusted under 35 U.S.C. 154(b) by 128 days.

This patent is subject to a terminal disclaimer.

(21) Appl. No.: 13/711,810

(22) Filed: Dec. 12, 2012

(65) Prior Publication Data

US 2013/0345450 A1    Dec. 26, 2013

Related U.S. Application Data

(60) Provisional application No. 61/569,793, filed on Dec. 13, 2011.

(51) Int. Cl.
  *C07D 307/46* (2006.01)
  *C07D 307/68* (2006.01)

(52) U.S. Cl.
  CPC ............ *C07D 307/46* (2013.01); *C07D 307/68* (2013.01)

(58) Field of Classification Search
  CPC ............................. C07D 307/46; C07D 307/68
  See application file for complete search history.

(56) References Cited

U.S. PATENT DOCUMENTS

| 2,929,823 | A * | 3/1960 | Garber et al. ................ 549/488 |
| 3,201,331 | A | 8/1965 | Hunter |
| 4,740,605 | A | 4/1988 | Rapp |
| 2012/0330035 | A1 | 12/2012 | Kindler et al. |
| 2012/0330039 | A1 | 12/2012 | Kindler et al. |
| 2013/0150596 | A1 | 6/2013 | Backes et al. |
| 2013/0150597 | A1 | 6/2013 | Backes et al. |

FOREIGN PATENT DOCUMENTS

| DE | 3601281 A1 | 7/1987 |
| EP | 0230250 A2 | 7/1987 |
| EP | 1834950 A1 | 9/2007 |
| EP | 1834951 A1 | 9/2007 |
| WO | WO-2012175584 A1 | 12/2012 |
| WO | WO-2012175650 A2 | 12/2012 |
| WO | WO-2013/087523 A1 | 6/2013 |
| WO | WO-2013/087613 A1 | 6/2013 |
| WO | WO-2013/087614 A1 | 6/2013 |

OTHER PUBLICATIONS

Descores et al. FR 2664273 A1, Jan. 10, 1992, machine translation.*
Glover, Selecting Evaporators for Process Applications, Reprinted from Chemical Engineering Progress, Dec. 2004.*
Lewkowski, ARKIVOC 2001 (i) 17-54.*
International Search Report in for PCT/ EP2012/074737, mailing date Mar. 26, 2013.
Kawamoto, H., "Catalytic Pyrolysis of cellulose in sulfolane with acidic catalysts", J Wood Sci., vol. 53, (2007), pp. 127-133.
Kazi, F., "Techno-economic analysis of dimethylfuran (DMF) and hydroxymethylfurfural (HMF) production from pure fructose in catalytic processes", Chemical Engineering Journal, vol. 169, (2011), pp. 329-338.
Mascal, M., et al., "Direct, High-Yield Conversion of Cellulose into Biofuel", Angew. Chem. Int. Ed., vol. 47, (2008), pp. 7924-7926.

* cited by examiner

*Primary Examiner* — Layla Bland
(74) *Attorney, Agent, or Firm* — Drinker Biddle & Reath LLP

(57) ABSTRACT

Method for producing solutions which comprise 5-hydroxymethylfurfural (HMF) and have a reduced content of starting materials of the HMF synthesis or a reduced content of by-products of the HMF synthesis (hereinbelow called product solution), which comprises treating solutions which comprise
  HMF
  starting materials or by-products of the HMF synthesis and
  an organic solvent having at least two ether groups (for short polyether)
(hereinbelow called starting solution) in an evaporator with steam.

17 Claims, 1 Drawing Sheet

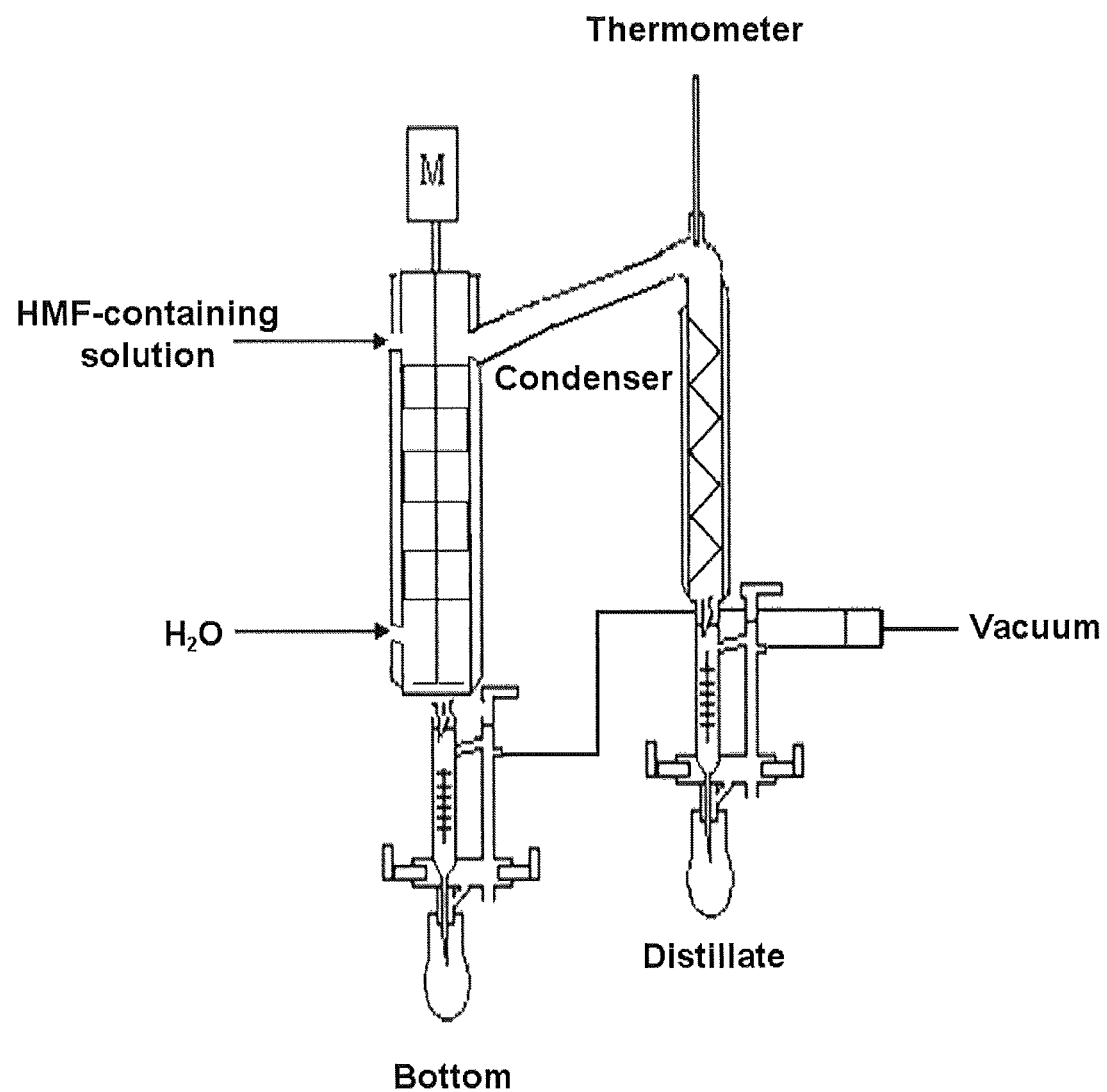

SEPARATING OFF 5-HYDROXYMETHYLFURFURAL (HMF) FROM REACTION SOLUTIONS BY STEAM DISTILLATION

RELATED APPLICATIONS

This application claims benefit (under 35 USC 119(e)) of U.S. Provisional Application Ser. No. 61/569,793, filed Dec. 13, 2011, which is incorporated herein by reference in its entirety.

BACKGROUND OF THE INVENTION

Description

The present invention relates to a method for producing solutions which comprise 5-hydroxymethylfurfural (HMF) and have a reduced content of starting materials of the HMF synthesis or a reduced content of by-products of the HMF synthesis (hereinbelow called product solution), which comprises treating solutions which comprise
  HMF
  starting materials or by-products of the HMF synthesis and
  an organic solvent having at least two ether groups (for short polyether)
(hereinbelow called starting solution) in an evaporator with steam.

Compounds which are obtained from renewable raw materials and can be converted easily by chemical reactions to compounds which can be used industrially are increasingly of importance for chemical syntheses.

In this connection, 5-hydroxymethylfurfural (HMF) is known; this can be produced from hexoses by various methods. For example, 2,5-furandicarboxylic acid is readily obtainable from HMF and is suitable as dicarboxylic acids for producing polymers, such as polyesters or polyurethanes, and can replace other dicarboxylic acids from non-renewable raw materials in industrial applications.

HMF is generally produced by acid-catalyzed dehydration of hexoses such as glucose or fructose.

The reaction product obtained is acidic solutions which, besides the HMF, comprise unreacted starting materials and/or by-products. During the HMF synthesis, as a rule only a partial conversion of the starting materials takes place in order to avoid the formation of by-products. In general, the solutions obtained therefore comprise unreacted starting materials such as hexoses or oligomers or polymers composed of hexoses. In the case of higher conversions, the amount of by-products increases.

Separating off the HMF from the reaction solution which comprise starting materials or by-products of the HMF synthesis is complex and hinders the accessibility of HMF.

For example, Feroz Kabir Kazi et al. describe in Chem. Eng. J. 169 (2011), pages 329-338 separating off the HMF from the acidic reaction solution by a complex extraction method using an organic solvent (butanol); a solution of HMF in butanol is obtained.

DE-A 3601281 discloses a chromatographic separation method in which firstly any organic solvents are removed and the aqueous HMF solution is separated using an ion exchange column. The HMF fraction obtained is crystallized.

A further method of separating off HMF from the reaction solution is the conversion of the HMF to another compound which is easier to separate off, optionally followed by a back-conversion to HMF after separation has taken place. For example, according to Mark Mascal and Edward B. Nikitin in 2008 Angew. Chemie vol. 47, pages 7924-7926, HMF is converted to the more stable 5-chloromethylfurfural and then converted again to HMF or derivatives thereof. Alternatively, according to EP-A 1834950, the ethers or, according to EP-A 1834951, the esters of HMF are produced which, after separation has taken place, are directly suitable for further syntheses.

Haru Kawamoto, Shinya Saito et al. describe in J. Wood Sci. (2007), 53, pages 127-133 the pyrolysis of cellulose with the formation of levoglucosenone, furfural and/or HMF under various conditions, including with the introduction of steam.

HMF should be present for further syntheses in the purest possible form. Of particular suitability for further syntheses are aqueous solution of HMF which does not comprise by-products or residual starting materials, or at best comprises them in very small amounts. Methods known hitherto for producing HMF or aqueous solutions thereof with adequate purity are extremely complex.

The object of the present invention was therefore a method with which HMF or aqueous solutions thereof can be provided in the purest possible form in as simple and effective a manner as possible.

Accordingly, the method defined at the start has been found.

A BRIEF DESCRIPTION OF THE FIGURE

FIG. 1 shows an apparatus comprising a thin-film evaporator and a device for condensation.

A DETAILED DESCRIPTION OF THE INVENTION

In the method according to the invention, HMF-containing starting solutions are subjected to a steam distillation in order, in so doing, to obtain HMF-containing production solutions with a reduced content of starting materials or by-products from the synthesis.

The Starting Solutions

Starting solutions are preferably solutions which are obtained during the production of HMF.

HMF is usually produced by acid-catalyzed dehydration of hexoses, e.g. glucose or in particular fructose. The hexoses can in turn be obtained from oligomeric or polymeric compounds such as starch, cellulose beforehand or in situ while carrying out the dehydration. By-products may be formed during the reaction.

The dehydration is preferably carried out in aqueous solution, although in principle it is also possible to use other solvents or mixtures of solvents.

The solutions obtained during the dehydration can therefore comprise a very wide variety of compounds, such as unreacted starting materials (hexoses, starch, celluloses), acid used as catalyst (for short acid catalyst), solvents or by-products of the HMF synthesis (carboxylic acids, HMF oligomers, so-called humins).

The solution obtained during the dehydration can, if desired, be worked-up prior to being used as starting solution, e.g. the solutions can be filtered in order to separate off solids. The solutions obtained can also already be free from acid. The latter is the case e.g. when heterogeneous acids have been used which can be separated off easily as solid or which were introduced during the reaction in a fixed bed and therefore do not enter the reaction solution.

Embodiments below relate to preferred compositions of the starting solution used for the steam distillation.

The starting solution comprises
HMF,
starting materials or by-products of the HMF synthesis and an organic solvent having at least two ether groups (in short polyether).

The starting solution comprises HMF usually in amounts of from 1 to 30% by weight, particularly preferably from 2 to 20% by weight, based on the total weight of the starting solution.

The starting solution can comprise starting materials of the HMF synthesis. The starting materials of the HMF synthesis are hexoses or oligomers or polymers composed of hexoses (hereinbelow called saccharides in summary).

The starting solution can therefore in particular comprise hexoses, oligomers or polymers composed of hexoses or both hexoses and oligomers or polymers composed thereof.

Preferred hexoses are fructose or glucose, in particular fructose or mixtures of fructose and glucose.

Oligomers or polymers of the hexoses are preferably starch or cellulose.

The content of saccharides in the starting solution overall is, in one particular embodiment, more than 0.1% by weight, in particular more than 0.5% by weight, preferably more than 1% by weight, based on the total weight of the starting solution.

The content of saccharides in the starting solution overall is in general not more than 20% by weight, in particular not more than 10% by weight, based on the total weight of the starting solution.

In particular, at least 50% by weight, in particular at least 70% by weight, of the saccharides present in the starting solution are hexoses, e.g. fructose or glucose, preferably fructose or mixtures of fructose and glucose with a fraction of more than 50% by weight of fructose.

The starting solution can comprise by-products of the HMF synthesis.

By-products, the content of which is reduced by the method according to the invention, are in particular HMF oligomers (so-called humins). The content of humins in the starting solution can be e.g. 0 to 10% by weight, in particular 0 to 5% by weight. In one particular embodiment, the starting solution comprises at least 0.05% by weight, in particular at least 0.1% by weight, of humins.

Other by-products are e.g. carboxylic acids, in particular formic acid, acetic acid, laevulinic acid or mixtures thereof.

The starting solution can also comprise acids which have been used as catalyst in the production of the HMF. In particular, these are acids dissolved in the starting solution (homogeneous acids). Heterogeneous acids (solids) which have been used as catalysts during the production of the HMF can be easily separated off beforehand or do not even enter the starting solution, as has already been described above.

Suitable (homogeneous) acids are any desired inorganic or organic acids. By way of example, mention may be made of para-toluenesulfonic acid, methanesulfonic acid ($MeOSO_3H$), oxalic acid, sulfuric acid, hydrochloric acid or phosphoric acid.

The content of all acids in the starting solution can be e.g. 0 to 10% by weight, based on the total weight of the starting solution.

As explained above, the starting solution comprises starting materials or by-products of the HMF synthesis. For example, the starting solution can comprise starting materials, but no by-products of the HMF synthesis; this can be the case for HMF syntheses with partial conversion. For example, the starting solution can comprise by-products of the HMF synthesis, but no starting material; this can be the case for HMF synthesis with complete conversion, although in this case by-products are then formed in larger amounts. In customary cases, the starting solution will, however, comprise both starting materials and also by-products of the HMF synthesis; in particular, it comprises both saccharides and humins, preferably in the amounts described in each case.

The starting solution comprises an organic solvent having at least two ether groups (for short polyether). The polyether can be added to the starting solution e.g. shortly before carrying out the method according to the invention; however, it can also have already been used as solvent in the solution during the production of the HMF and therefore already be present in the starting solution.

The polyether preferably has a boiling point greater than 250° C. (standard pressure, 1 bar).

The polyether preferably has a melting point of less than 60° C., in particular of less than 30° C. (at standard pressure, 1 bar); the polyether is particularly preferably liquid at 20° C. (standard pressure).

The polyether preferably comprises at least 3, in particular at least 4, particularly preferably at least 6, ether groups. In general, it comprises not more than 40, in particular not more than 30, ether groups, particularly preferably not more than 20 ether groups.

In a particular embodiment, the polyether comprises no heteroatoms apart from oxygen in the form of ether groups and optionally hydroxyl groups.

In particular, it is an aliphatic polyether, particularly preferably a polyalkylene glycol, in which case the terminal hydroxyl groups can be etherified with alkyl groups, in particular C1- to C4-alkyl groups.

The alkylene groups of the polyalkylene glycols may be e.g. C2- to C10-, in particular C2- to C4-alkylene groups, such as ethylene, propylene or butylene groups. The polyethers can also comprise different alkylene groups, e.g. in the form of blocks.

Very particular preference is therefore given to poly-C2- to C4-alkylene glycols, in particular polyethylene glycol, the terminal hydroxyl groups of which can be optionally etherified with alkyl groups; the number of repeat alkylene ether groups corresponds to the above number of ether groups, in particular the number of repeat alkylene ether groups is 4 to 30, particularly preferably 6 to 20. The terminal hydroxyl groups of the polyether can be etherified with alkyl groups, in particular C1- to C4-alkyl groups.

The starting solution comprises the polyether preferably in amounts of from 5 to 90% by weight, in particular from 30 to 80% by weight, particularly preferably from 50 to 70% by weight.

The starting solution is preferably an aqueous solution since the production of HMF preferably takes place in water. Alternatively, the production of HMF is also possible in organic solvents, meaning that the starting solution can optionally also comprise organic solvents of this type. These are, for example, polar aprotic solvents such as DMSO, MIBK, MEK, 2-MeTHF, and also protic solvents, in particular alcohols, ethers, polyethers or polyalkylene glycols (see above).

Preferably, the content of organic solvents other than polyethers (or polyalkylene glycols) in the starting solution is less than 20% by weight, in particular less than 10% by weight and particularly preferably less than 5% by weight.

Preferred starting solutions comprise e.g.

| | |
|---|---|
| 1 to 30% by weight | of HMF |
| 1 to 20% by weight | of saccharides |
| 0 to 10% by weight | of humins (by-product of the HMF synthesis) |
| 5 to 90% by weight | of polyethers |
| 0 to 40% by weight | of water |
| 0 to 30% by weight | of other constituents, such as acids, organic solvents other than polyethers etc. | based on the total weight of the solution.

Steam Distillation

The treatment of the starting solution with steam is a steam distillation known per se.

The treatment of the starting solution with steam takes place preferably at reduced pressure, in particular a pressure of from 1 to 300 mbar is contemplated. In particular, the pressure in the evaporator is 1 to 100 mbar, particularly preferably 1 to 50 mbar and, in a very particularly preferred embodiment, 1 to 40 or 1 to 35 mbar.

The treatment of the starting solution with steam takes place preferably at a temperature of the starting solution of from 100 to 200° C., particularly preferably from 120 to 180° C. and particularly preferably from 140 to 180° C. and very particularly preferably 150 to 180° C.

Preferably, the method according to the invention is operated continuously.

To this end, the starting solution and the steam are fed to the evaporator continuously and the product solution is drawn off continuously.

The volume streams depend on the size of the evaporator and separation efficiency of the selected type of evaporator.

In a preferred embodiment, the ratio of the supplied volume of steam to the volume of supplied starting solution is in a range from 0.5 to 2 volume units of steam per 1 volume unit of starting solution, particularly preferably in the range from 0.8 to 1.5 volume units of steam per 1 volume unit of starting solution and in particular 0.8 to 1.2 volume units of steam per 1 volume unit of starting solution.

Suitable evaporators are customary evaporators which are set up for the introduction of starting solution and steam and in particular for the continuous procedure described above.

Preferred evaporators are thin-film evaporators. In these, the starting solution is present in the evaporator as a liquid film.

Particular preference is given to vertical thin-film evaporators; vertical thin-film evaporators of this type are known under equipment names such as "Luwa" or in particular "Sambay".

The preferred vertical thin-film evaporators are ultimately a perpendicular tube with internal devices for distributing and mixing the starting solution and external devices for heating the tube wall.

The starting solution is preferably fed in the upper part of the thin-film evaporator and distributed as film on the heated tube wall. Steam can be fed to the evaporator, preferably to the thin-film evaporator, together with the starting solution or at any other desired point of the evaporator. The starting solution and the steam can be passed to the evaporator in the same direction (cocurrent) or in the opposite direction (countercurrent).

Preferably, the steam is supplied countercurrently to the starting solution. For this purpose, the starting solution is fed in particular in the upper part of the evaporator, and the steam is fed in in the lower part of the evaporator.

The steam and the volatile constituents of the starting solution are preferably discharged via a separator at the top of the evaporator and condensed (product solution).

The nonvolatile constituents pass through the evaporator and are separated off as a liquid bottom product.

FIG. 1 shows a corresponding apparatus consisting of thin-film evaporator (Sambay) and device for the condensation.

Product Solution

The product solution obtained after condensation comprises the HMF separated off from the starting solution.

It is one advantage of the method according to the invention that HMF can be separated off from the starting solution easily, effectively and in a large amount.

In particular, the product solution comprises more than 70%, particularly preferably more than 85%, particularly preferably more than 95% of the HMF which has been fed to the evaporator via the starting solution.

At the same time, the product solution obtained has a high purity.

In particular, it comprises no, or at best only small, amounts of the polyether. The content of polyether in the product solution is in particular less than 5% by weight, preferably less than 2% by weight and particularly preferably less than 1 or less than 0.5% by weight, based on the total weight of the product solution.

In particular, the content of saccharides in the product solution is considerably reduced compared with the content of the saccharides in the starting solution, and/or saccharides are not present, or are barely still present in the product solution. In particular, the percentage content of all saccharides in the product solution is in total less than 20%, in particular less than 10%, of the content of all saccharides in the starting solution.

Preferably, the product solution comprises less than 5% by weight, in particular less than 2% by weight, particularly preferably less than 1% by weight, very particularly preferably less than 0.5% by weight, of saccharides, and, in a particular embodiment, less than 0.1% by weight of saccharides, based on the total weight of the product solution.

In particular, the content of humins in the product solution is also considerably reduced compared to the content of the humins in the starting solution, and/or humins are not present, or are barely still present, in the product solution. In particular, the percentage content of all humins in the product solution is in total less than 20%, in particular less than 10%, of the content of the humins in the starting solution.

Preferably, the product solution comprises less than 5% by weight, in particular less than 2% by weight, particularly preferably less than 1% by weight, very particularly preferably less than 0.5% by weight of humins, and, in a particular embodiment, less than 0.1% by weight of humins, based on the total weight of the product solution.

As a result of the method according to the invention, in particular product solutions are obtained in which saccharides and humins are not detectable or are barely still detectable, and their content is in total below 0.5, in particular below 0.1 or below 0.05% by weight.

In particular, starting solutions are, as a result of their content of humins, dark or black, whereas the product solutions obtained are clear and light.

The product solution is suitable for chemical syntheses in which HMF is used as starting material. In particular, the product solution is suitable for chemical syntheses in which the starting material HMF is desired or required in high purity. By way of example, mention be made here of the use of the product solution for producing 2,5-furandicarboxylic acid or 2,5-bis(hydroxymethyl)furan.

EXAMPLES

Example 1

Synthetic Mixtures without Sugar

Starting Solution

The starting solution was obtained by mixing pure substances.

It comprises from 2-10% by weight of HMF in a mixture of water/high-boiling components.

The high-boiling components used were:
DMSO: dimethyl sulfoxide
PEG-400: a polyethylene glycol with a molecular weight of 400
PEG-600: a polyethylene glycol with a molecular weight of 600
Tetraglyme: tetraethylene glycol dimethyl ether
Carrying Out the Steam Distillation The steam distillation is carried out in the apparatus as in FIG. 1. The apparatus consists of a glass Sambay, which is operated in countercurrent procedure.

The starting solution was fed in at the top, and the steam was fed in the lower third.

The composition of the product solution for various high-boiling components and also the selected temperatures and pressures are listed in the table. The stated temperature is that of the heating medium at the external wall of the tube, which is a good approximation to that of the liquid film of the starting solution at the internal wall of the tube.

The experiments were carried out continuously; each new temperature and pressure adjustment was followed by a waiting period until a steady state was reached.

The composition was determined by means of HPLC. The stated yield of HMF is the percentage fraction of the HMF in the distillate or in the bottom, based on the HMF content (=100%) in the starting solution. If the sum of the HMF content in the distillate and bottom deviates somewhat from 100, this is caused by a measurement error.

TABLE 1

Continuous experiments with mixtures of pure substances

| High-boiling component | Temperature [° C.] | Pressure [mbar] | HMF yield [%] Distillate | Bottom |
|---|---|---|---|---|
| DMSO | 160 | 250 | 100 | 0[1] |
| DMSO | 160 | 200 | 100 | 0[1] |
| DMSO | 160 | 160 | 100 | 0[1] |
| DMSO | 160 | 135 | 100 | 0[1] |
| PEG-400 | 160 | 120 | 46 | 19 |
| PEG-400 | 160 | 80 | 64 | 7 |
| PEG-400 | 160 | 35 | 86 | 3 |
| PEG-600 | 140 | 200 | 83 | 17 |
| PEG-600 | 140 | 120 | 74 | 28 |
| PEG-600 | 140 | 80 | 55 | 48 |
| PEG-600 | 140 | 50 | 66 | 37 |
| PEG-600 | 160 | 80 | 81 | 11 |

TABLE 1-continued

Continuous experiments with mixtures of pure substances

| High-boiling component | Temperature [° C.] | Pressure [mbar] | HMF yield [%] Distillate | Bottom |
|---|---|---|---|---|
| PEG-600 | 160 | 50 | 88 | 2 |
| PEG-600 | 160 | 25 | 99 | 2 |

[1]with DMSO as added solvent, no bottom was obtained; the total amount of HMF, DMSO and water is in the distillate.

Example 2

Synthetic Mixtures with Sugar

Starting Solution

The starting solution was obtained by mixing pure substances.

It comprised ca. 6% by weight of HMF and 3% by weight of fructose in a water/high-boiling component mixture.

Using this new starting solution, steam distillation was carried out as is described in example 1. In each case, the content of HMF and of fructose in the distillate (product solution) and in the bottom was determined.

It can be established that at all settings a distillate is obtained which is virtually free from fructose. As the temperature decreases, more HMF passes over into the distillate.

It may be noted that the distillate (product solution) comprises introduced steam and the concentrations of distillate and bottom therefore do not add up to the concentration of the starting solution.

TABLE 2

Continuous experiments with mixtures of pure substances, including sugar

| High-boiling component | Temperature [° C.] | Pressure [mbar] | HMF [% by wt] in the Distillate | Bottom | Fructose [% by wt.] in the Distillate | Bottom |
|---|---|---|---|---|---|---|
| PEG-600 | 140 | 200 | 0.66 | 3.39 | 0.00 | 1.71 |
| PEG-600 | 140 | 120 | 1.31 | 3.34 | 0.00 | 1.95 |
| PEG-600 | 140 | 80 | 2.09 | 2.69 | 0.00 | 2.08 |
| PEG-600 | 140 | 25 | 3.48 | 0.43 | 0.02 | 2.63 |
| PEG-600 | 160 | 200 | 2.50 | 2.21 | 0.00 | 1.31 |
| PEG-600 | 160 | 120 | 3.37 | 0.99 | 0.01 | 1.40 |
| PEG-600 | 160 | 80 | 4.45 | 0.56 | 0.02 | 1.29 |
| PEG-600 | 160 | 25 | 3.53 | 0.11 | 0.04 | 1.79 |

Example 3

Actual Reaction Discharges

Using the starting solution below obtained from the HMF synthesis, the steam distillation was carried out as is described in example 1. In each case, the content of HMF and of fructose in the distillate (product solution) and in the bottom was determined.

The starting solution was obtained by reaction of fructose in a water/high-boiling component mixture with p-toluene-sulfonic acid as catalyst at 160° C.

It comprised (after neutralization) HMF, fructose (for precise content see legend) and also other secondary components in a water/high-boiling component mixture.

| High-boiling component | Temperature [° C.] | Pressure [mbar] | HMF yield [%] Distillate | HMF yield [%] Bottom | HMF [% by wt.] in the Distillate | HMF [% by wt.] in the Bottom | Fructose [% by wt.] in the Distillate | Fructose [% by wt.] in the Bottom |
|---|---|---|---|---|---|---|---|---|
| Tetraglyme[a] | 160 | 140 | 30 | 70 | 0.98 | 3.70 | 0.00 | 0.19 |
| Tetraglyme[a] | 160 | 80 | 78 | 13 | 1.68 | 1.82 | 0.00 | 0.26 |
| PEG-600[b] | 160 | 25 | 78 | 0 | 0.61 | 0.00 | 0.00 | 0.24 |
| PEG-600[c] | 160 | 40 | 97 | 8 | 4.63 | 0.49 | 0.06 | 11.10 |

[a]3.13% by weight of HMF, 0.26% by weight of fructose
[b]1.15% by weight of HMF, 0.23% by weight of fructose
[c]3.94% by weight of HMF, 7.62% by weight of fructose The yield of HMF stated in the table refers to the HMF present in the starting solution. The sum of the HMF yield in the distillate and bottom does always give 100% since HMF from the starting solution can polymerize to a small degree to give humins, as a result of which the yields are less than 100%. If fructose is also present, additional HMF can be formed in small amounts, as a result of which the yields can be greater than 100%.

The starting solution was colored black on account of the content of humins. The product solution obtained was clear with a very slight yellowish tinge. The product solution was therefore essentially free from humins.

The invention claimed is:

1. A method for producing solutions which comprise 5-hydroxymethylfurfural (HMF) and have a reduced content of starting materials of the HMF synthesis or a reduced content of by-products of the HMF synthesis (hereinafter called product solution), which comprises treating solutions which comprise
   HMF
   starting materials or by-products of the HMF synthesis and
   an organic solvent having at least two ether groups (for short polyether)
(hereinafter called starting solution) in an evaporator with steam.

2. The method of claim 1, wherein the starting materials of the HMF synthesis are hexoses or oligomers or polymers composed of hexoses (hereinafter called saccharides).

3. The method of claim 1, wherein the by-products of the HMF synthesis are HMF oligomers.

4. The method of claim 1, wherein the polyether has a boiling point greater than 250° C., at standard pressure.

5. The method of claim 1, wherein the polyether is a poly-C2- to C4-alkylene glycol, the terminal hydroxyl groups of which are optionally etherified with C1-C4 alkyl groups.

6. The method of claim 1, wherein the starting solution comprises the polyether in amounts of from 5% to 90% by weight.

7. The method of claim 1, wherein the starting solution is an aqueous solution.

8. The method of claim 1, wherein the treatment with steam takes place at 100° C. to 200° C.

9. The method of claim 1, wherein the treatment with steam takes place at a pressure of from 1 mbar to 300 mbar.

10. The method of claim 1, wherein the method is carried out continuously, such that the starting solution and steam are fed to the evaporator continuously and the product solution is drawn off continuously.

11. The method of claim 1, wherein the evaporator is a thin-film evaporator.

12. The method of claim 1, wherein the steam is fed countercurrent to the starting solution.

13. The method of claim 1, wherein the percentage content of all saccharides in the product solution is in total less than 20% of the content of all saccharides in the starting solution.

14. A process for producing 2,5-furandicarboxylic acid or 2,5-bis(hydroxymethyl)furan which comprises producing a product solution by the process of claim 1 and synthesizing 2,5-furandicarboxylic acid or 2,5-bis(hydroxymethyl)furan from the product solution.

15. The process according to claim 1, wherein the product solution comprises at least 70% of the HMF of the starting solution.

16. The process according to claim 1, wherein the ratio of volume of steam to volume of starting solution is from 0.5:1 to 2:1.

17. The process according to claim 1, further comprising discharging the steam and the volatile constituents of the starting solution via a separator at the top of the evaporator and condensing the volatile constituents to form the product solution.

* * * * *